United States Patent [19]

Edinburgh et al.

[11] Patent Number: 5,123,284
[45] Date of Patent: Jun. 23, 1992

[54] METHOD AND APPARATUS FOR MESUREMENT OF TENSION IN AN ELASTIC SURFACE

[76] Inventors: John D. Edinburgh, 2106 Turtle Creek Dr., Missouri City, Tex. 77459; Curtis D. Johnson, 6003 Spring Creek Ln., Spring, Tex. 77379

[21] Appl. No.: 588,345
[22] Filed: Sep. 26, 1990
[51] Int. Cl.$^5$ ................................. G01N 3/08
[52] U.S. Cl. .......................... 73/826; 73/159
[58] Field of Search ............ 73/826, 862.43, 838, 73/840, 159, 862.48, 862.45, 862.47

[56] References Cited

U.S. PATENT DOCUMENTS 2,674,127  4/1954  Garrett et al. ............. 73/862.48 X

FOREIGN PATENT DOCUMENTS 1307251  4/1987  U.S.S.R. ................. 73/862.48
115338  5/1918  United Kingdom ............ 73/862.47

Primary Examiner—Jerry W. Myracle
Attorney, Agent, or Firm—Kenneth A. Roddy

[57] ABSTRACT

A method and apparatus are disclosed for the measurement of tension in a stretched elastic surface. The apparatus includes a rigid housing having at least two diametrically opposed sides and a spring device contained therein with a contact member connected to the spring device which protrudes a predetermined distance outwardly beyond the ends of the housing sides when the spring device is in a resting state. Measuring and display devices are connected to the spring device for measuring the spring deflection when the housing is pressed against an elastsic surface. The housing is placed adjacent the elastic surface to be measured with the contact member in contact with the elastsic surface such that a fixed distance exists between the ends of the housing sides and the surface prior to application of a pressing force. The housing is then pressed against the elastic surface until the ends of the housing sides come into contact with the surface such that the spring device is deflected. The deflection is measured and displayed as an indication of the tension in the elastic surface. In one embodiment the spring device is a cantilever beam with the measuring device being at least one strain gauge mounted thereon. In another embodiment, the spring device is a coil spring with the measuring device being a linear variable differential transformer.

9 Claims, 5 Drawing Sheets

METHOD AND APPARATUS FOR MESUREMENT OF TENSION IN AN ELASTIC SURFACE

BACKGROUND OF THE INVENTION

1. Field of the Invention

This invention relates generally to methods and apparatus for the measurement of tension in elastic surfaces which are being held in a stretched state, and more particularly to the measurement of tension in thin, plane surfaces such as may be composed of the strings of sporting rackets, continuous plastic or paper sheet, or thin stretched, flexible surfaces of various composition.

2. Brief Description of the Prior Art

The present invention is concerned with surfaces composed of either continuous or discontinuous material which has been placed under tension. Such surfaces are employed in a vast array of settings in the consumer and industrial world. In many cases it is desirable and/or necessary to have knowledge of the tension under which the surface has been placed. The present invention was devised to provide a simple, portable, hand-held method of making such a measurement, and which is also non-invasive, i.e., not requiring the surface to be broken.

A common example in the consumer sector is the stringed surface of sporting rackets. This includes tennis, racketball, squash and badminton as the more commonly known sports employing such rackets. Knowledge of the tension of the strings in these rackets is important to the successful employment of the racket in competition. No simple, reliable and portable method is presently known to exist which allows the competitor to measure the tension of the racket. Players presently rely of subjective determination by "plucking" the strings and listening to the frequency of the resulting string vibration. Some devices have been made with attempt to measure the tension from such frequency, but these have been of limited accuracy and usefulness.

Examples in the industrial sector include the need for tension measurement of continuous sheets of plastic, either during the manufacture of the plastic or during employment for packaging. The tension of paper during production or employment, as in printing operations, is also measured.

Individuals skilled in specific arts related to consumer and industrial operations will identify many other instances wherein the measurement of surface tension is desired or required.

Existing surface tension measurement systems are contained for example in U.S. Pat. No. 3,739,633 to Saxl. The device presented in that patent is based upon squeezing the material between fixed and flexible members and measuring the force on the flexible member. The device must be used near an edge and must fit on both sides of the surface. The device and method are most suited to rolling stock measurement, such as magnetic tape, and would be unsuitable for the strings of sporting rackets.

Other tension measurement systems such as U.S. Pat. No. 4,821,583 to Richards and U.S. Pat. No. 4,759,226 to Leurer are specific to the measurement of tension in thread or lines of any composition. The principles of these systems depend upon thread stock producing a force on a force resistance element, such as a spring plate or cantilever beam. These systems could not be employed for the measurement of surface tensions as for example in the mesh structure of rackets.

The present invention is distinguished over the prior art in general, and these patents in particular by a method and apparatus for the measurement of tension in a stretched elastic surface which utilizes a rigid housing having at least two diametrically opposed sides and a spring device contained therein with a contact member connected to the spring device which protrudes a predetermined distance outwardly beyond the ends of the housing sides when the spring device is an a resting state. Measuring and display devices are connected to the spring device for measuring the spring deflection when the housing is pressed against an elastic surface. The housing is placed adjacent the elastic surface to be measured with the contact member in contact with the elastic surface such that a fixed distance exists between the ends of the housing sides and the surface prior to application of a pressing force. The housing is then pressed against the elastic surface until the ends of the housing sides come into contact with the surface such that the spring device is deflected. The deflection is measured and displayed as an indication of the tension in the elastic surface. In one embodiment the spring device is a cantilever beam with the measuring device being at least one strain gauge mounted thereon. In another embodiment, the spring device is a coil spring with the measuring device being a linear variable differential transformer.

SUMMARY OF THE INVENTION

It is therefore an object of the present invention to provide a method and apparatus for the measurement of tension in elastic surfaces which are being held in a stretched state.

It is another object of this invention to provide a method and apparatus for the measurement of tension in thin, plane surfaces such as the strings of sporting rackets, continuous plastic or paper sheet, or the thin stretched, flexible surface of any composition.

Another object of this invention is to provide a measurement device which can be adjusted to measure tension of surfaces of very high or very low tension.

Another object of this invention is to provide a portable, compact, hand-held device for measuring tension in an elastic surface.

A further object of this invention is to provide a device for measuring tension in elastic surfaces which is quickly and easily applied on only one side of the surface, on any part of the surface, and can be used for static surfaces or moving surfaces.

A still further object of this invention is to provide a device for measuring tension in elastic surfaces which is simple in construction, economical to manufacture, and rugged and accurate in use.

Other objects of the invention will become apparent from time to time throughout the specification and claims as hereinafter related.

The above noted objects and other objects of the invention are accomplished by a method and apparatus for the measurement of tension in a stretched elastic surface which utilizes a rigid housing having at least two diametrically opposed sides and a spring device contained therein with a contact member connected to the spring device which protrudes a predetermined distance outwardly beyond the ends of the housing sides when the spring device is in a resting state. Measuring and display devices are connected to the spring device for measuring the spring deflection when the housing is pressed against an elastic surface. The housing is placed adjacent the elastic surface to be measured with the contact member in contact with the elastic surface such that a fixed distance exists between the ends of the housing sides and the surface prior to application of a pressing force. The housing is then pressed against the elastic surface until the ends of the housing sides come into contact with the surface such that the spring device is deflected. The deflection is measured and displayed as an indication of the tension in the elastic surface. In one embodiment the spring device is a cantilever beam with the measuring device being at least one strain gauge mounted thereon. In another embodiment, the spring device is a coil spring with the measuring device being a linear variable differential transformer.

DESCRIPTION OF THE PREFERRED EMBODIMENT

Figure 1:
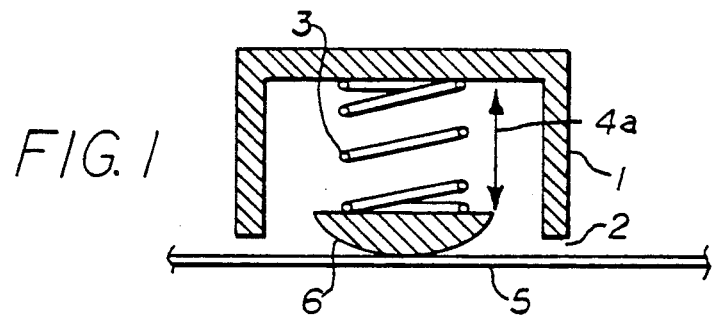
FIG. 1 is a cross section illustrating schematically a device employing the principles of measurement embodied in the present invention.

The present invention utilizes the principle that tension in the surface to be measured can be determined by the deflection experienced by a mechanical spring, internal to the measurement device, so long as certain geometric considerations are maintained. The measurement devices described hereinafter are pressed in a prescribed manner against the surface whose tension is to be measured. This pressing causes deflection of an internal spring assembly. Measurement of the spring deflection allows determination of the surface tension.

The physical principles upon which this invention is based is contained in the following description. First, for small deflections, a spring is defined as a physical device which follows Hooke's Law, wherein the amount of deflection is linearly proportional to a force applied, to compress or extend the spring. The constant of proportionality is referred to as the spring constant and is typically related to the dimensions of the spring and the physical properties of the material from which the spring is constructed. Hooke's Law is expressed in general as, $$F = -Sx \qquad (1)$$

where F is the force applied, S the spring constant, and x the spring displacement.

Second, a surface under tension can be deflected by application of a force normal to the surface. For small deflections this action can also be modeled as a spring for which the surface deflection at the point of force application is linearly related to the applied normal force. The constant of proportionality in this case is simply related to the tension in the surface. The relationship between applied force, F, normal surface deflection, y, and the tension, T, is given by, $$F = -kTy \qquad (2)$$

where k is a constant number related to surface material.

Thirdly, when two springs are placed in series and a force is applied, each will deflect by an amount determined by their respective constants of proportionality. This means that the total deflection is shared in a proportional way between the two springs. The spring with the greater constant of proportionality will deflect the least.

The first principle feature of the present invention is that the method is so defined that when a device employing the method is pressed against the surface the internal spring and surface act like two springs in series. Therefore each experiences a deflection in accordance with their respective constants of proportionality and the applied force. The constant of proportionality of the spring is fixed while that of the surface depends upon its tension.

The second principle feature of the present invention is that devices using the method are configured and used in such a way that the sum of the internal spring deflection and the surface deflection is always the same, regardless of the tension of the surface. This means that in every application a fixed amount of deflection will be shared in a proportional fashion between the internal spring and the surface.

Suppose the designed total deflection is given by X. Then the sum of the internal spring deflection, x, and surface deflection, y, must equal X. From this fact and Equations (1) and (2) a general relation between surface tension and internal spring deflection can be found.

$$T = \frac{Sx}{k(X - x)} \qquad (3)$$

For a surface of infinite tension all of the deflection of the system will occur in the internal spring, which will thus experience maximum deflection. From Equation (3), if x=X, then the tension is infinite.

At the other extreme, for a surface of tension going to zero, the deflection will all occur in the surface and the internal beam will not be deflected at all. From Equation (3), if x=0 then the tension is zero.

All other values of surface tension between zero and infinity will result in specific values of internal spring deflection between zero and X. Therefore a method of measuring surface tension is realized by measurement of the internal spring deflection.

Many means can be found to configure the internal spring and measure its deflection in various devices using this method but all depend on the basic relationship of Equation (3) relating internal spring deflection to surface tension.

One preferred embodiment of the measuring device uses a cantilever beam as the internal spring element. A cantilever beam can be modeled as a spring in that there is a linear relation between deflection of the beam and applied force. The spring constant is related in a simple and well known way to the dimensions of the beam and the modulus of elasticity of the beam material. Beam deflections are easily measured by mounting strain gauges on the beam near the region of maximum strain.

Another embodiment of the measuring device uses a standard coil spring as the internal spring. In this case deflection of the internal spring can be measured by many means such as a linear variable differential transformer (LVDT) connected between the spring and the housing.

The basic operation of the measuring device is best described with reference to FIGS. 1 and 2 which illustrate somewhat schematically a simplified model of the device in cross-section. The physical shape of the housing 1 can be of any geometry such as rectangular, square or circular. The internal spring 3 is shown as a coil spring for the purpose of description but any system which obeys Hooke's Law can be used. The housing 1 is of any rigid material which will not deflect or deform under the application of forces on the order of the tension to be measured. The spring 3 is firmly attached to the housing 1. A foot 6 is used for contact with the surface whose tension is to be measured. The foot is shown as a half spherical shape but can be of any shape. The foot can be made of any rigid material which will not appreciably deform under the application of forces on the order of the tension to be measured, such as rigid plastic, wood or metal for example.

In FIG. 1 the assembly is shown in the resting state, in contact with the elastic surface 5 whose tension is to be measured, but exerting no force on that surface. The distance 2 between the housing 1 and the surface 5 is fixed by the physical structure of the system and is the same for every application of measurement. The resting length of the spring 4a is determined by the mechanical design of the spring.

Figure 2:
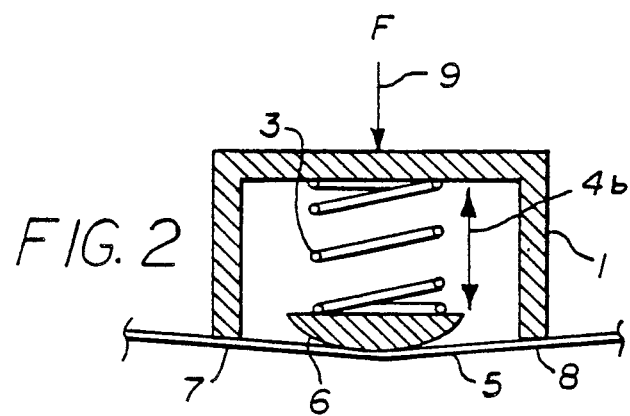
FIG. 2 illustrates the device of FIG. 2 having been pressed in the prescribed manner against the elastic surface whose tension is to be measured.

FIG. 2 shows the results of application of a force 9 pushing the housing 1 against the elastic surface 5. The value of the force 9 is not important so long as it is sufficient to create contact between the surface 5 and housing 1 at points 7 and 8. Thus the gap 2 of FIG. 1 has gone to zero. The internal spring 3 has compressed to a new length 4b. The difference between the resting length 4a and compressed length 4b is the deflection of the internal spring 3. Note that total deflection is shared between the spring 3 and the surface 5, but that this total must sum to the gap distance 2.

The conditions of FIG. 2 satisfy those of equation (3) above. The internal spring 3 deflection can be measured by many suitable means, examples of which are presented herein. Since the total deflection is given by the resting gap 2 the surface tension can be found from the known parameters of the spring and surface.

Figure 3A:
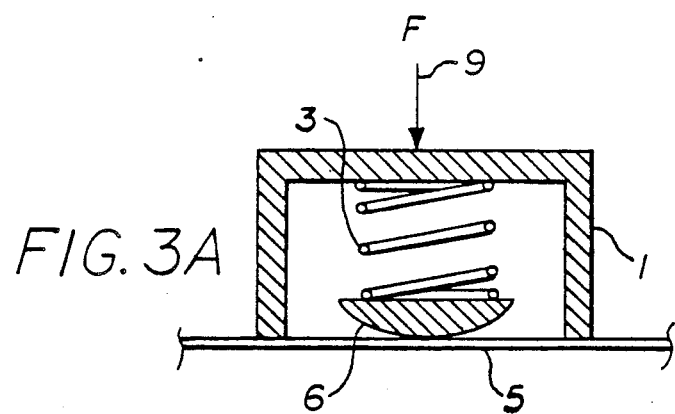
FIG. 3A illustrates the device of FIG. 2 pressed against a surface of infinite tension.
Figure 3B:
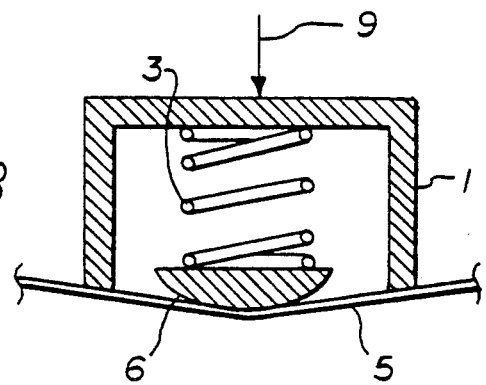
FIG. 3B illustrate the device of FIG. 2 pressed against a surface of zero tension.

FIG. 3A shows a measurement condition for a surface of very large tension. In this case all the deflection has occurred in the internal spring 3 and none in the surface 5. FIG. 3B shows a measurement condition at the other extreme of a surface of very little tension. In this case all the deflection has occured in the surface 5 and none in the internal spring 3.

Figure 4:
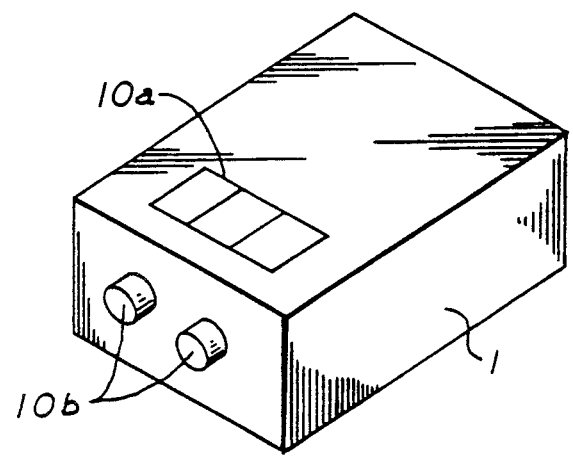
FIG. 4 is an isometric view of a measurement device in accordance with a preferred embodiment of the present invention taken from the top.

FIG. 4 shows a top view of a preferred tension measuring device based upon the measurement method disclosed herein. The housing 1 is shown in square configuration although it can be of any shape, such as rectangular or circular. The housing 1 can be made of any rigid material such as metal or plastic. A multi-digit, electronic readout 10a is used to present the tension of the surface to the user. Assorted conventional electronic controls, such as on/off switches and zeroing knobs are indicated by 10b. Other electronic controls or cables for connection to remote readouts or computer data acquisition systems may be used as desired in particular applications.

Figure 5:
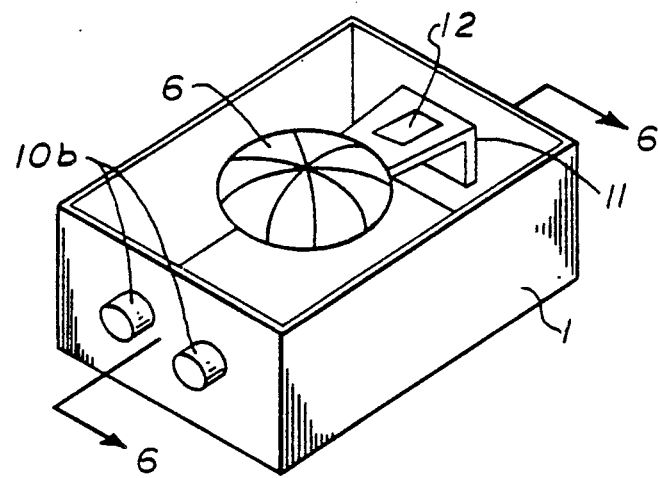
FIG. 5 is an isometric view inverted to show the bottom of the embodiment of FIG. 4 which uses a cantilever beam for the internal spring.

The essential features of one preferred embodiment of the device are best seen in the bottom view in FIG. 5. In this embodiment the internal spring is a cantilever beam 11. Such a cantilever beam can be modeled as a spring in terms of the deflection of the beam for application of bending forces to the unrestrained end. The foot 6 used to push against the surface is shown as a half spherical shape for this presentation but any shape can be used. The foot 6 can be made of any rigid material such as metal, plastic or hard wood.

The cantilever beam 11 is bent into the shape of an "L" so that it can be attached to the inside of the housing 1. Any other method of attaching the beam can be used so long as it provides a secure bonding of the beam 11 to the housing 1. The beam is made of a particular metal and with dimensions to provide deflections suitable to the range of surface tension to be measured.

The foot 6 is firmly attached to the beam 11 so that if a force is applied to the foot the beam will deflect. Strain gauges 12 and 14 (not visible in this view) are attached to the beam to measure its deflection.

Figure 6:
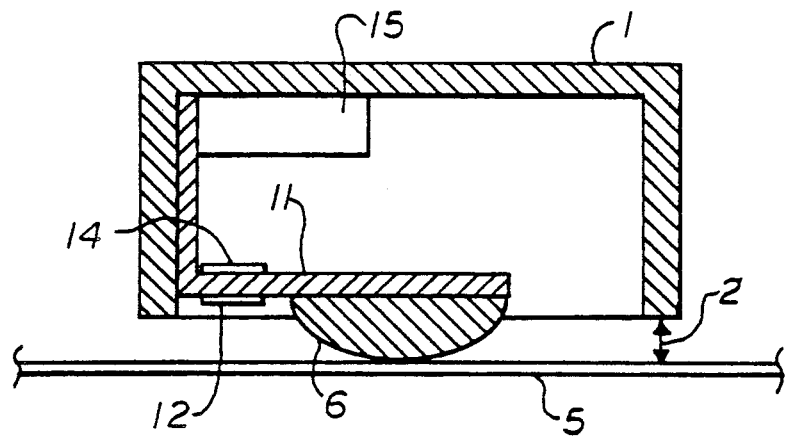
FIG. 6 is a cross section taken along the line 6—6 of FIG. 5 of the device placed in contact with a surface but prior to applying a force.

As seen in cross section in FIG. 6, the foot 6 is placed in contact with a surface 5, but not exerting any force on the surface. A fixed distance 2 is shown between the surface 8 and the lower edge of the housing 1. This distance is fixed by the geometry of the device. The required electronics 15 are shown as is necessary to convert the output of the strain gauges 12 and 14 to a user visible readout 10a.

Figure 7:
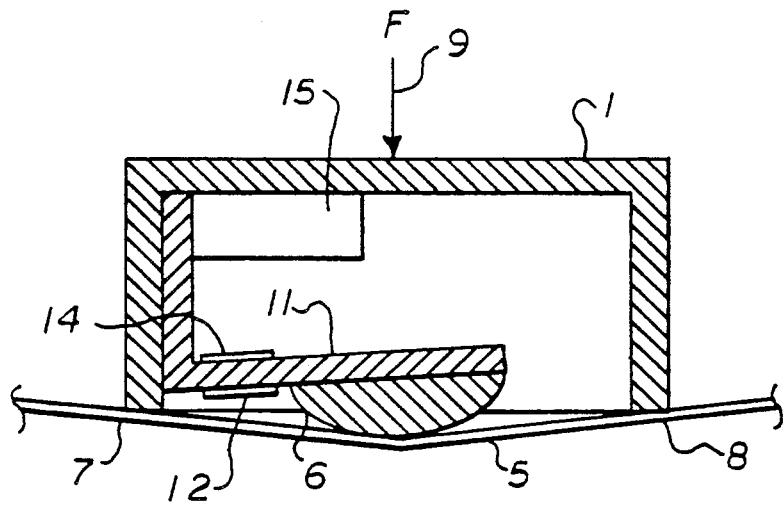
FIG. 7 is a cross section similar to FIG. 6 of the device in use measuring the tension of some surface.

As shown in FIG. 7, the housing 1 has been forced down with a force 9 until contact has been made between the surface and the housing edges a 7 and 8. Notice that the surface 5 has experienced some deflection and the beam 11 has also experienced some deflection. The sum of these two deflections will be the "resting" distance 2 between the housing 1 and surface 5. The beam deflection causes a proportional strain in the beam. This strain is converted into resistance change by the strain gauge 12 and 14. The electronics 15 converts the resistance change into a calibrated tension readout for the user.

By selection of various beam 11 dimensions and material and by selection of an appropriate resting distance 2 the device can be tailored to measure any required range of tensions, as appropriate for different surfaces.

The force 9 required to press the housing against the surface can be provided by any convenient means. In many cases the device can be hand-held and pressed against the surface using the force of human arms until edge contact at 7 and 8 is made. This would be the case for sporting rackets for example. When used to measure high tensions, as in an industrial setting, the force 9 can be provided by electric, pneumatic or hydraulic motors which press the device against the surface until edge contact at 7 and 8 is made.

Figure 9:
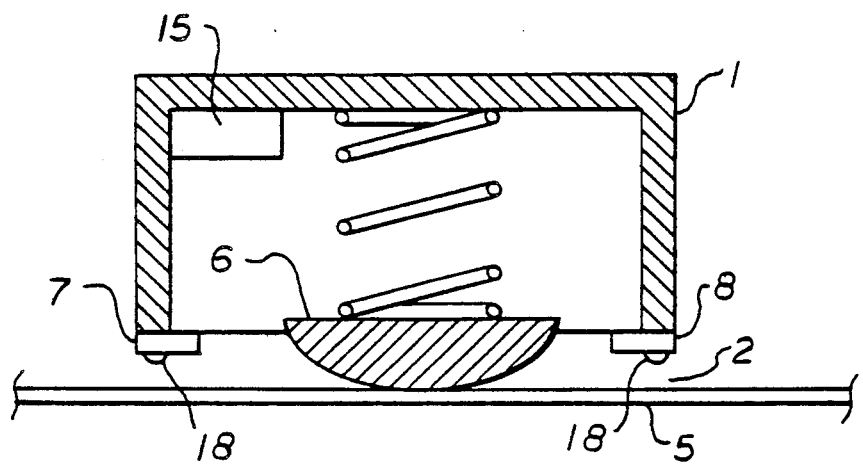
FIG. 9 is a cross section of a modification of the measuring device having switches mounted on the device to detect surface contact.

Contact with the surface 7 and 8 can be determined by visual examination or using contact switches mounted on the housing 1 at the contact edges 7 and 8 (FIG. 9). Actually once contact has been made between the surface 5 and the housing 1, as at 7 and 8, further increases of force 9 will cause no significant increase in deflection of the beam 11. Thus contact at 7 and 8 is also indicated when the deflection of the beam 11 stabilizes. The electronics can be so designed that when the strain signal stops variation as the force 9 is slowly increased, the necessary deflection 2 has occured and a readout is presented.

Figure 8:
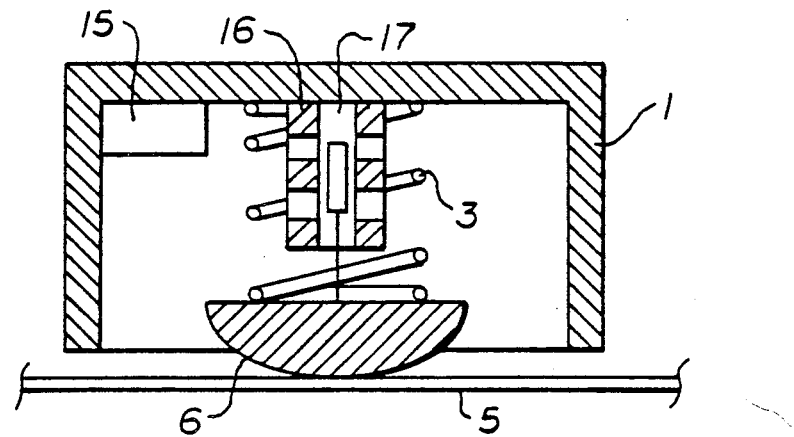
FIG. 8 is a cross section of another embodiment of the measuring device using a coil spring and LVDT to measure deflection.

FIG. 8 shows another embodiment of the tension measuring device using a linear variable differential transformer (LVDT) to measure spring deflection. In this embodiment the internal spring is a coil spring 3 firmly attached to the housing 1 and the contact foot 6. In this case the LVDT coils 16 are solidly fixed to the housing 1. The LVDT core 17 is likewise attached to the foot 6. Any deflection of the spring 3 from pressing the device against an elastic surface 5 will cause a displacement between the LVDT core 17 and coils 16. Conventional electronics 15 will convert the resulting LVDT output into an appropriate readout for the user.

As seen in FIG. 9, the measuring device may also have switches 18 mounted on the contact edges 7 and 8 of the housing 1 to detect surface contact. The switches 18 are coupled to the electronic readout 15 to provide evidence that displacement at 2 has occured and that a reading of the tension can be taken. One or more sets of switches may be used to assure flush contact has been made between the housing surface 7 and 8 and the elastic surface 5.

Figure 10:
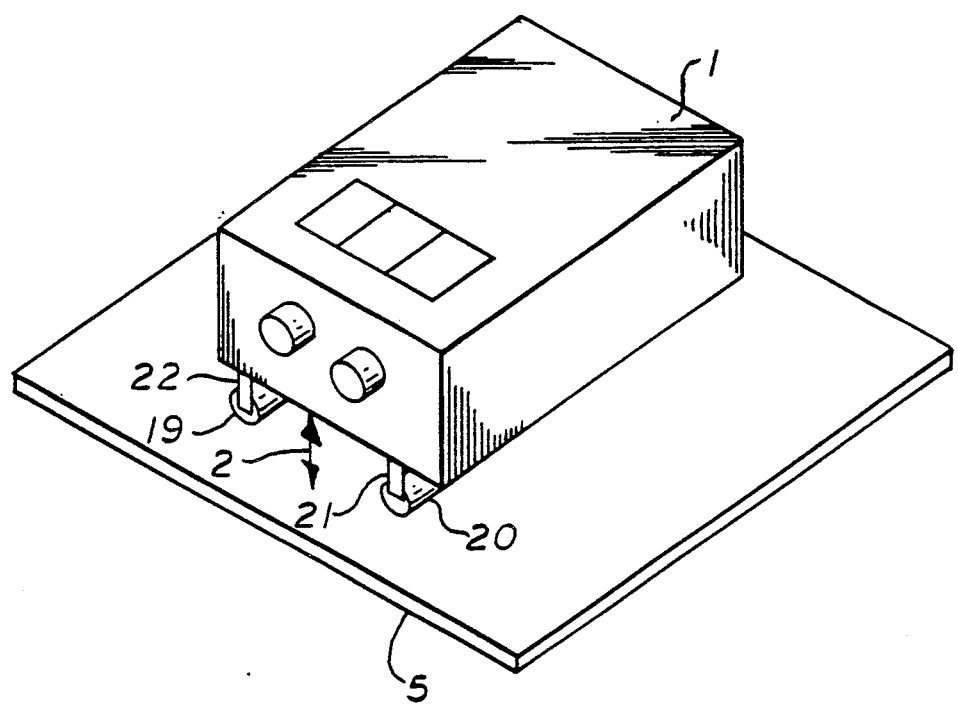
FIG. 10 is an isometric view of another modification of the measuring device having rollers mounted thereon to facilitate the measure of deflection in a moving elastic surface.

FIG. 10 shows another modification of the measuring device having rollers 19 and 20 mounted on supports 21 and 22 at the bottom of contact edges 7 and 8 of the housing 1 to facilitate the measure of deflection in a moving elastic surface. The roller supports 21 and 22 may be slidably connected to the housing 1 so as to engage contact switches coupled to the readout electronics to indicate when the gap 2 has been closed and that a tension reading can be taken on the moving elastic surface 5.

While this invention has been described fully and completely with special emphasis upon several preferred embodiments, it should be understood that within the scope of the appended claims the invention may be practiced otherwise than as specifically described herein.

We claim:

1. An apparatus for measuring the tension in a elastic surface comprising;
    a rigid housing having at least two diametrically opposed sides for contacting an elastic surface having a constant of proportionality dependent upon its surface material and the tension of which is to be measured,
    spring means having a predetermined constant of proportionality secured within said housing and having a free end,
    contact means connected to the free end of said spring means and protruding a predetermined distance outwardly beyond the ends of said housing sides for contacting the elastic surface to be measured when said spring means is in a resting state and deflecting said spring means upon sufficient force,
    measuring means including display means operatively connected with said spring means for measuring the spring deflection when said housing is pressed against the elastic surface, such that
    when said housing is placed adjacent an elastic surface to be measured with said contact means in contact with the surface a fixed distance will exist between the ends of the housing sides and the surface prior to application of a pressing force, and
    upon pressing said housing against the elastic surface until the ends of said housing sides come into contact with the surface said contact means will cause deflection of said spring means which is measured by said measuring means and displayed as an indication of the tension in the elastic surface,
    the tension of the elastic surface relative to deflection of said spring means being determined by the equation;

$$T = \frac{Sx}{k(X - x)}$$

where
T = tension of the elastic surface,
X = total deflection,
x = deflection of said spring means,
S = the spring constant, and
k = a constant number related to surface material.

2. An apparatus according to claim 1 wherein
said spring means comprises a cantilever beam, and
said measuring means comprises at least one strain gauge mounted on said cantilever beam.

3. An apparatus according to claim 1 wherein
said spring means comprises a coil spring, and
said measuring means comprises a linear variable differential transformer.

4. An apparatus according to claim 1 including
contact switch means on the ends of said housing sides coupled to display means for indicating contact between said housing and the surface to be measured.

5. An apparatus according to claim 1 including
roller means on the ends of said housing sides, and
roller means on said contact means, whereby
said housing may be pressed against a moving elastic surface to be measured without undo friction.

6. An apparatus according to claim 1 wherein
said contact means comprises a semi-spherical member of rigid material having an outwardly curved surface for contacting the elastic material.

7. An apparatus according to claim 1 wherein
said housing comprises a box-like member having opposed side walls and at top wall.

8. A method of measuring the tension in a elastic surface comprising the steps of;
    providing rigid housing having at least two diametrically opposed sides and spring means contained therein with contact means connected to said spring means and protruding a predetermined distance outwardly beyond the ends of said housing sides when said spring means is in a resting state and measuring means including display means operatively connected to said spring means for measuring the spring deflection when said housing is pressed against an elastic surface, said spring means having a predetermined fixed constant of proportionality and said elastic surface having a constant of proportionality dependent upon the tension in its surface material, placing said housing adjacent the elastic surface to be measured with said contact means in contact with the surface such that a fixed distance exists between the ends of the housing sides and the surface prior to application of a pressing force, pressing said housing against the elastic surface until the ends of said housing sides come into contact with the surface such that said contact means will cause deflection of said spring means, and measuring the deflection of said spring means and displaying the measurement as an indication of the tension in the elastic surface, the tension of the elastic surface relative to deflection of said spring means being determined by the equation;

$$T = \frac{Sx}{k(X - x)}$$

where

T = tension of the elastic surface,
X = total deflection,
x = deflection of said spring means,
S = the spring constant, and
k = a constant number related to surface material.

9. The method according to claim 8 wherein the steps of measuring the deflection of said spring means and indicating the tension of the elastic surface comprise;

determining the total deflection of said spring means and said elastic surface when the force is applied, and determining the respective proportion of the total deflection for said spring means and for said elastic surface wherein the constant of proportionality of said spring means is fixed while that of the elastic surface is dependent upon its tension, and calibrating and measuring the deflection of said spring means when the force is applied, such that said spring means will experience maximum deflection when forced against an elastic surface of infinite tension with the result representing infinite tension in the elastic surface, and when forced against an elastic surface of zero tension, the deflection will occur in the elastic surface and the spring means will experience no deflection with the result representing zero tension in the elastic surface, and all other values of surface tension between zero and infinity will result in specific values of internal spring deflection between zero and infinity which will correspond to the surface tension of the elastic surface being measured.

* * * * *